(12) United States Patent
Berg

(10) Patent No.: US 7,368,592 B1
(45) Date of Patent: May 6, 2008

(54) PROCESS FOR THE PREPARATION OF ALKYL N-ALKYLANTHRANILATE

(75) Inventor: Carsten Berg, Borre (DK)

(73) Assignee: Prom Limited, Surrey (GB)

( * ) Notice: Subject to any disclaimer, the term of this patent is extended or adjusted under 35 U.S.C. 154(b) by 783 days.

(21) Appl. No.: 10/381,923

(22) PCT Filed: Oct. 4, 2000

(86) PCT No.: PCT/GB00/03808

§ 371 (c)(1),
(2), (4) Date: May 5, 2003

(87) PCT Pub. No.: WO02/28818

PCT Pub. Date: Apr. 11, 2002

(51) Int. Cl.
*C07C 229/00* (2006.01)
*C07D 215/00* (2006.01)
(52) U.S. Cl. .......................................... 560/19; 546/155
(58) Field of Classification Search .................. 560/19; 546/155
See application file for complete search history.

(56) References Cited

U.S. PATENT DOCUMENTS 2,967,128 A    1/1961   Kare ............................ 167/46
4,633,009 A    12/1986  Lerner ......................... 560/19

FOREIGN PATENT DOCUMENTS

| DE | 39 36 229 | 5/1991 |
| GB | 1 549 297 | 8/1979 |
| GB | 2 236 318 | 4/1991 |
| IN | 14-6359 | 7/1977 |

OTHER PUBLICATIONS

EP 135367, Mar. 27, 1985, p. 1.*
Aldrich, 1998-1999, pp. 654 and 1154. (3 pages).*
Staiger, J.Org Chem(1959), 24, 1214-1219.
Hardtmann, J. Heterocycl.Chem. (1975), 12(3), 565-72.
J Singh, Indian J. Chem. vol. 20B, 1981 pp. 596-597.
The International Search Report dated Jun. 28, 2001.

* cited by examiner

*Primary Examiner*—Taylor Victor Oh
(74) *Attorney, Agent, or Firm*—Nields & Lemack

(57) ABSTRACT

This invention is directed to a process of preparing alkyl N-alkylanthranilate, specially Methyl N-methylanthranilate, represented by Formula (I), in a one pot synthesis, using available and cheap commercial chemicals such as Isatoic anhydride, solid sodium hydroxide, dimethyl sulfate and methanol. Purity of the crude product is about 97% and yield 85%.

14 Claims, No Drawings

PROCESS FOR THE PREPARATION OF ALKYL N-ALKYLANTHRANILATE

TECHNICAL FIELD OF THE INVENTION

The invention relates to a process for the preparation of alkyl N-alkylanthranilate of the Formula 1.

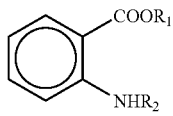

Formula 1

More particularly it is concerned with the preparation of Methyl N-methylanthranilate, Formula 1, $R_1=R_2=Me$.

BACKGROUND OF THE INVENTION

Methyl N-methylanthranilate (DMA) is a valuable compound used in the flavouring and fragrance industry and is also reported to be a bird repellent described in patent U.S. Pat. No. 2,967,128.

Several methods are known for the preparation of DMA.

A classical route is N-methylation of methyl anthranilate with a methylating agent as dimethyl sulfate or methyl iodide, cited in patent DE 3936229. To avoid dimethylation, reductive methylation with formaldehyde and hydrogen has been described in patent U.S. Pat. No. 4,633,009. Reaction scheme 1.

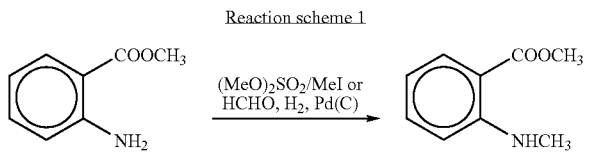

Reaction scheme 1

To prepare methyl anthranilate, 2H-3,1-benzoxazine-2,4 (1H)-dione (isatoic anhydride) is reacted under alkaline conditions with methanol as disclosed in patent IN 146359. Reaction scheme 2.

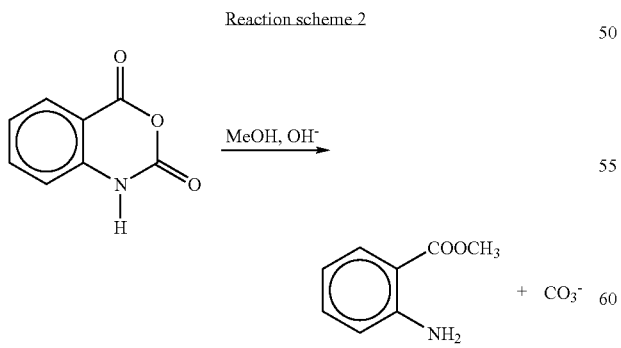

Reaction scheme 2

As disclosed by Staiger, J. Org. Chem. (1959), 24, 1214-19, N-methylisatoic anhydride reacts with methanol under alkaline conditions to produce Methyl N-methylanthranilate.

Hardtmann, J. Heterocycl. Chem. (1975), 12 (3), 565-72 prepares N-substituted isatoic anhydride by reacting the N-sodium salt of isatoic anhydride, prepared from sodium hydride, with alkyl halides. The N-benzyl derivative of isatoic anhydride is prepared using potassium carbonate and benzyl chloride.

DISCLOSURE OF INVENTION

It is an object of this invention to provide a facile process for the preparation of N-alkyl alkylanthranilates, specially N-methyl methyl anthranilate, in commercial quantities, good yield and high purity.

An obvious route would be a one pot synthesis starting with the ready available isatoic anhydride, N-alkylation and final reaction with an alcohol to furnish the title product.

Surprisingly it turned out that a solid metal hydroxide or basic metal oxide, preferable sodium or potassium hydroxide in a suitable polar solvent such as dimethylforamide or 1-methyl-2-pyrrolidinone could form the N-metal salt with isatoic anhydride.

Depending on solvent, concentration or temperature the metal salt would separate to form a dispersion.

One would anticipate that water formed during the salt formation immediately would react with isatoic anhydride, forming anthranilic acid.

Surprisingly this was not the case.

Trials using metal alkoxides resulted in that the alkohols formed, reacted with isatoic anhydride to form alkyl esters of anthranilic acid.

N-methylation could be achieved by adding an alkylation agent. Preferably methyl iodide or dimethyl sulfate in a molar ratio, relative to isatoic anhydride, from 1 to 5, preferably 1.5, at a temperature from 10-40° C. In the case of a methylating agent, the intermediate N-methylisatoic anhydride could be isolated by filtration as a colourless crystalline compound by adding 2 parts of water to the reaction mixture. Identification was established by compare HPLC chromatograms with authentic material (supplied by Aldrich).

After N-alkylation of isatoic anhydride has been performed 1 to 50 mole parts of an alkyl alkohol, relative to isatoic anhydride, is added to the reaction mixture at a temperature between 10 and 40° C. The temperature is elevated to distil excess of alkyl alcohol off. Leaving 50% to 0% of the alcohol in the reaction mixture. Preferably 10%.

By alcohol addition under alkaline conditions, N-alkylisatoic anhydride, is ring opened, forming alkyl N-alkylanthranilate with subsequent elimination of carbon dioxide.

Alkyl N-alkylanthranilate is isolated by adding 1 to 5 parts of water to the reaction mixture, and extract the mixture with a non water miscible organic solvent.

The extraction solvent could be an alicyclic or cyclic hydrocarbon, halogenated derivatives hereof, aliphatic ethers or esters. Preferably hexane.

The organic phase is washed with water, and evaporated in vacuo, leaving alkyl N-alkylanthranilate as an oil with purity about 97% and yield about 85%.

EXAMPLES

Products were analysed by gas chromatography. Using SRI Instruments model 310 equipped with column Restek, MXT-5, 15 m, 0.54 ID, FID detector and temperature gradient 90-200° C., 10°/min.

Peaks were identified by running authentic samples.

Example 1

Methyl N-methylanthranilate

To dry Dimethylforamide (DMF), 300 mL, covered with nitrogene, solid pulverised sodium hydroxide, 97% assay, 14.12 g, 0.3424 moles, is added.

Isatoic anhydride, 96% assay, 40.00 g, 0.2354 moles, is dissolved in dry DMF, 100 mL.

To the stirred suspension of sodium hydroxide covered with nitrogen, the solution of isatoic anhydride is added at 30° C. over 30 min. and the mixture is stirred for a further 15 min.

Dimethyl sulfate, 32.88 g, 0.2588 moles is added drop wise with stirring over 20 min., allowing temperature to rise to max 45° C. The solution is stirred at ambient temperature for a further 30 min.

Methanol, 50 mL, is added, the mixture is stirred for 15 min at 25° C. Temperature is elevated to distil methanol off. When temperature reaches 100° C., the mixture is cooled to 20° C. and water, 800 mL is added. Ammonia solution, 2 mL, 25 w/w % is added to destroy excess dimethyl sulfate. P The cloudy mixture is extracted with hexane, 200 mL. The hexane phase is separated, washed with water and distilled on a rotary evaporator at 15 mm Hg and 100° C. leaving crude Methyl N-methylanthranilate, 33.80 g, with a composition, by GC, of 2.1% Methyl anthranilate and 97.5% Methyl N-methylanthranilate, corresponding to a yield of the theoretical of 85%.

Crude Methyl N-methylanthranilate, 33.80 g, is distilled through a 30 cm Vigreux column at 130-131° C. at 15 mm Hg, giving 28.10 g Methyl N-methylanthranilate with a composition, by GC, of 1.5% Methyl anthranilate and 98.5% Methyl N-methylanthranilate.

Example 2

To dry Dimethylforamide (DMF), 75 mL, covered with nitrogene, solid pulverised potassium hydroxyde, 85% assay with 15% water, 5.80 g, 0.0879 moles, is added. Isatoic anhydride, 96% purity, 10.00 g, 0.0588 moles, is dissolved in dry DMF, 35 mL.

To the stirred suspension of potassium hydroxide covered with nitrogen, the solution of isatoic anhydride is added at 30° C. over 30 min. and the mixture is stirred for a further 15 min.

Methyl iodide, 12.50 g, 0.0883 moles is added drop wise with stirring over 20 min., allowing temperature to rise to max 40° C. The solution is stirred at ambient temperature for a further 30 min.

Methanol, 50 mL, is added, the mixture is stirred for 15 min at 25° C.

Temperature is risen so methanol is distilled off. When temperature reaches 100° C., the mixture is cooled to 20° C. and water, 200 mL is added, and the mixture is extracted with 2 times hexane. The combined hexane phases are washed with water and distilled on a rotary evaporator at 15 mm Hg and 100° C. leaving crude Methyl N-methylanthranilate, 8.10 g, with a composition, by GC, of 4.4% Methyl anthranilate and 95.3% Methyl N-methylanthranilate, corresponding to a yield of the theoretical of 80%.

The invention claimed is:

1. A process for the preparation of an alkyl ester of N-alkyl anthranilic acid represented by Formula 1:

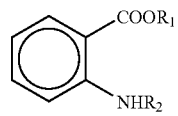

Formula 1 wherein $R_1$ and $R_2$ independent represent alkyl groups, by reacting 2H-3,1-benzoxazine-2,4(1H)-dione (isatoic anhydride) in a polar aprotic organic solvent as medium, with a solid metal hydroxide or basic metal oxide, adding an alkylating agent to form an N-alkyl intermediate and thereafter reacting the intermediate with an alkyl alcohol to form a reaction mixture containing the product of Formula 1.

2. A process according to claim 1, wherein the product according to Formula 1 is isolated by adding water to the reaction mixture and is extracted with a non-water miscible apolar organic extraction solvent.

3. A process according to claim 1, wherein said polar solvent is selected from the group consisting of a carboxamide, a nitrile, an ether, a sulphoxide and hexaalkyl phosphoric triamide.

4. A process according to claim 1, wherein said solid metal hydroxide or basic metal oxide is selected from the group consisting of hydroxides and oxides of Li, Na, K, Ca and Ba.

5. A process according to claim 1, wherein said alkylating agent is selected from alkyl halides, wherein the alkyl group has from 1 to 8 carbon atoms and wherein the halide is selected from the group consisting of Cl, Br and I.

6. A process according to claim 1, wherein said alkylating agent is selected from dialkyl esters of sulfuric acid (dialkyl sulfates), wherein the alkyl groups have from 1 to 8 carbon atoms and is selected from the group consisting of non-substituted alkyl groups.

7. A process according to claim 1, wherein said alkyl alcohol is selected from the group consisting of primary, secondary, and tertiary alcohols all with a maximum of 8 carbon atoms.

8. A process according to claim 2, wherein said extraction solvent is selected from the group consisting of $C_{5-10}$ linear, branched and cyclic alkanes.

9. A process according to claim 2, wherein said extraction solvent is hexane.

10. A process according to claim 1, wherein said polar solvent is selected from the group consisting of dimethyl formamide and 1-methyl-2-pyrrolidinone.

11. A process according to claim 1, wherein said solid metal hydroxide or basic metal oxide is selected from the group consisting of sodium hydroxide and potassium hydroxide.

12. A process according to claim 1, wherein said alkylating agent is dimethyl sulfate.

13. A process according to claim 1, wherein said alkyl alcohol is methanol.

14. A process according to claim 1, wherein $R_1$ and $R_2$ are each a methyl group.

* * * * *